United States Patent
Bartek et al.

(10) Patent No.: US 6,673,957 B2
(45) Date of Patent: Jan. 6, 2004

(54) METHOD FOR PRODUCING ALKOXY MALONIC ACID DINITRILES

(75) Inventors: Johannes Bartek, Visp (CH); Rudolf Fuchs, Sion (CH); Stefan Hildbrand, Riehen (CH)

(73) Assignee: Lonza AG, Basel (CH)

( * ) Notice: Subject to any disclaimer, the term of this patent is extended or adjusted under 35 U.S.C. 154(b) by 0 days.

(21) Appl. No.: 10/182,716

(22) PCT Filed: Feb. 9, 2001

(86) PCT No.: PCT/EP01/01505
§ 371 (c)(1),
(2), (4) Date: Oct. 11, 2002

(87) PCT Pub. No.: WO01/58857
PCT Pub. Date: Aug. 16, 2001

(65) Prior Publication Data
US 2003/0144538 A1 Jul. 31, 2003

Related U.S. Application Data
(60) Provisional application No. 60/267,087, filed on Feb. 7, 2001.

(30) Foreign Application Priority Data
Feb. 10, 2000 (EP) .............................. 00102758
May 4, 2000 (EP) ............................. 00109505

(51) Int. Cl.[7] .......................................... C07C 255/04
(52) U.S. Cl. ..................... 558/460; 558/461
(58) Field of Search ................. 558/460, 461

(56) References Cited

FOREIGN PATENT DOCUMENTS

WO   WO-A-98/31652   7/1998

OTHER PUBLICATIONS

Monatsh. Chem., 1965, 96, 1677–1689.
Ibrahim, N.S., et al., Heterocyles, 1984, 22(8), 1677–1682.
Fairley, T.A., et al., J. Med. Chem., 1993, 36(12), 1746–1753.
Mohareb, R.M., et al., Z. Naturforsch. B. Anorg. Chem. Org. Chem., 1986, 41(1), 105–109.
Nemoto, Hisao, et al., J. Org. Chem., vol. 55, No. 15, (1990), pp. 4515–4516.
Nomoto, Hisao, et al., Tetrahedron Letters, vol. 40, No. 7, (Feb. 12, 1999), pp. 1319–1322.
Colson Abstract, Database Crossfire Beilstein Online, Database–Accession No. 199759, XP002165047 (1897).
Colson, M.A., Bulletin de la Societe Chimique de France, vol. 3., No. 13, (1985), pp. 231–237.
Colson, M.A., Ann. Chem. (Paris), Ser. 7, vol. 12, (1897), pp. 231–257.
Jammot, Jaqueline, et al., Database Crossfire Beitslein "Online", Database–Accession No. 1886581, ZP002165048 (1990).
Jammot, Jaqueline, et al., J. Chem. Soc., Perkins Transactions 2, vol. 1, (1990), pp. 157–162.

Primary Examiner—Alan L. Rotman
Assistant Examiner—Ebenezer Sackey
(74) Attorney, Agent, or Firm—Fisher, Christen & Sabol

(57) ABSTRACT

A method for producing alkoxy malonic acid dinitrites of general formula (I),

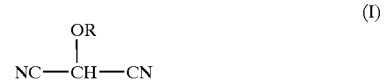

wherein $R^1$ means $C_{1-6}$-alkyl or halogen-substituted $C_{1-6}$-alkyl. The method involves converting the corresponding alkoxy malonic acid diamides of general formula (II),

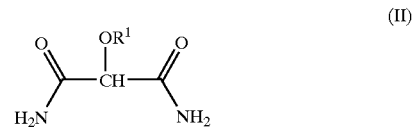

wherein $R^1$ has the aforementioned meaning, by means of a dehydrating agent. The intermediate products of general formula (III),

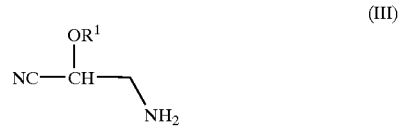

whereby the products are formed during dehydration.

7 Claims, No Drawings

METHOD FOR PRODUCING ALKOXY MALONIC ACID DINITRILES

This is a national stage application of International Application No. PCT/EP01/01505, filed on Feb. 9, 2001, that has benefit of U.S. Provisional Application No. 60/267,087, filed on Feb. 7, 2001, that has priority benefit of European Patent Application No. 00109505.8, filed on May 4, 2000, and that has priority benefit of European Patent Application No. 00102758.0, filed on Feb. 10, 2000.

The invention relates to a process for preparing alkoxymalononitriles.

International patent application WO-A-98/31652 describes the preparation of the anesthetic sevoflurane (fluoromethyl 1,1,1,3,3,3-hexafluoro-2-propyl ether) by reacting methoxymalononitrile with bromine trifluoride. However, WO-A-98/31652 does not disclose the preparation of methoxymalononitrile.

It is accordingly an object of the present invention to provide a process for preparing alkoxymalononitriles.

According to the invention, this object is achieved by the process according to claim 1.

It has been found that alkoxymalononitriles of the general formula

where $R^1$ is $C_{1-6}$-alkyl or halogen-substituted $C_{1-6}$-alkyl can be prepared by reacting the appropriate alkoxymalonamides of the general formula

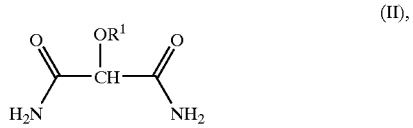

where $R^1$ is as defined above with a dehydrating agent.

"$C_{1-6}$-alkyl" are here and hereinbelow all linear or branched alkyl groups having 1–6 carbon atoms, for example methyl, ethyl, propyl, isopropyl, butyl, isobutyl, sec-butyl, tert-butyl, pentyl, isopentyl, tert-pentyl, neopentyl, hexyl or isohexyl.

"Halogen-substituted $C_{1-6}$-alkyl" are $C_{1-6}$-alkyl groups which are mono- or polysubstituted by halogen. Preferred halogens are fluorine, chlorine and bromine. Particular preference is given to fluorine. Examples include: mono-, di- or trifluoromethyl, chloromethyl, bromomethyl, 1- or 2-fluoroethyl, 1- or 2-chloroethyl, 1- or 2-bromoethyl and 1-, 2- or 3-fluoropropyl.

The $R^1$ radical is preferably methyl or trifluoromethyl.

Examples of useful dehydrating agents include trifluoroacetic anhydride, dibutyltin oxide, phosphorus oxychloride, phosphorus trichloride and phosphorus pentachloride. Preference is given to trifluoroacetic anhydride and phosphorus oxychloride.

The dehydrating agent is advantageously used in quantities of from 0.5 to 6 molar equivalent per amide group of the alkoxymalonamide of the formula II.

The dehydration is advantageously carried out in a suitable solvent. Examples of useful solvents include acetonitrile, dioxane, 1,2-dichloroethane, toluene, cyclohexane, heptane and octane. Preference is given to acetonitrile.

Preference is given to carrying out the dehydration in boiling solvent.

The dehydration is optionally carried out in the presence of a Lewis acid. Examples include the following Lewis acids: $BF_3$, $BCl_3$, $BBr_3$, $BI_3$, $SbF_5$, $AlCl_3$, $AlBr_3$, $TiBr_4$, $TiCl_4$, $TiCl_3$, $ZrCl_4$, $PF_5$, $FeCl_3$ and $FeBr_3$.

Preference is given to using $AlCl_3$ as the Lewis acid. The quantity of Lewis acid is preferably from 0.01 to 0.05 molar equivalent.

The compounds of the formula II can be prepared by known processes. For example, Monatsh. Chem., 1965, 96, 1677–1689 describes a process for preparing alkoxymalonamides by reacting methyl alkoxyacetates with dialkyl oxalates and reacting the product (dialkyl alkoxymalonate) with liquid ammonia.

The dehydration according to the invention proceeds in two stages, and the intermediate product formed is the corresponding 2-cyano-2-alkoxyacetamide of the general formula

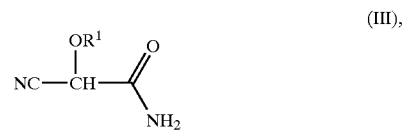

where $R^1$ is as defined above.

The 2-cyano-2-alkoxyacetamide (III) may be isolated or the dehydration reaction can be continued until the reaction product of the formula I is obtained.

To isolate the 2-cyano-2-alkoxyacetamide (III), the progress of the dehydration reaction is followed, for example by means of thin layer chromatography. The reaction is stopped at a suitable time, for example by cooling the boiling reaction mixture to 50–0° C., preferably to about 0° C.

The workup is effected by known methods, for example by means of extraction in the presence of a base and subsequent chromatography. An example of a useful base is sodium hydrogencarbonate.

The compounds of the formula III are chiral. They may be either in the S-configuration or the R-configuration. The above-described dehydration results in the racemate which may be separated into the two isomers by known processes, for example by HPLC chromatography using a column having a chiral stationary phase. Chiral stationary phases are known and commercially available, for example from E. Merck, Waters, Daicel or Macherey & Nagel.

The compounds of the formula III are novel and likewise form part of the subject-matter of the invention.

The compounds of the formula III can be converted in a similar manner to 2-cyanoacetamide, for example using 2-mercaptobenzoic acid to prepare 2-(4-oxobenzothiazin-2-yl)acetamide (N. S. Ibrahim et al., Heterocycles 1984, 22(8), 1677–1682), using 1,2-diaminobenzene to prepare benzimidazol-2-yl-acetonitrile (T. A. Fairley et al., J. Med. Chem. 1993, 36(12), 1746–1753) or using 2-cyanothioacetamide to prepare thiopyridines (R. M. Mohareb et al., Z. Naturforsch. B. Anorg. Chem. Org. Chem. 1986, 41(1), 105–109). Equally, the compounds of the formula III are useful for preparing barbiturates, coumarins or vitamins in a similar manner to the known use of 2-cyanoacetamide.

The examples hereinbelow illustrate the process according to the invention.

EXAMPLE 1

Preparation of Methoxymalononitrile in the Presence of $POCl_3$ 13.62 g (87.0 mmol) of $POCl_3$ and 0.3 g (2.3 mmol) of $AlCl_3$ were added to a solution of 10.0 g (75.7 mmol) of methoxymalonamide in 50 ml of acetonitrile and the reaction mixture was heated to reflux for 4 h. The solvent was distilled off, water was added and the aqueous phase extracted using diethyl ether (3×50 ml). The organic phase was dried and the solvent taken off on a rotary evaporator. Purification of the residue (7.28 g) by means of Kugelrohr distillation (110° C./20 mbar) delivered 4.42 g (61%) of methoxymalononitrile as a colorless liquid.

| | |
|---|---|
| $^1$H NMR (CDCl$_3$): δ = | 5.26 (s, 1H); 3.65 (s, 3H). |
| $^{13}$C NMR (CDCl$_3$): δ = | 110.12 (C≡N); 57.58 (CH$_3$); 57.33 (CH). |

EXAMPLE 2

Preparation of Methoxymalononitrile in the Presence of Trifluoroacetic Anhydride In a 250 ml round-bottom 3-neck flask, 10 g (75.7 mmol) of methoxymalonamide, 22 g (278 mmol) of pyridine and 100 ml of dioxane were initially charged under argon. At 2–5° C., 48.3 g (230 mmol) of trifluoroacetic anhydride were added dropwise. The reaction mixture was allowed to react at room temperature for 24 h. Afterwards, 200 ml of water and then 200 ml of methylene chloride were added at 10° C. After the phase separation, extraction was effected once more using 200 ml of methylene chloride. The combined organic phases were concentrated, and the resulting oily crude product (7 g) was distilled (27–30° C./1.6 mbar).

Yield: 2.6 g; 33%

EXAMPLE 3

2-Cyano-2-methoxyacetamide 6.74 g (44 mmol) of POCl$_3$ and 152 mg (1.14 mmol) of AlCl$_3$ were added to a solution of 5.0 g (38 mmol) of methoxymalonamide in 100 ml of acetonitrile at room temperature. This mixture was then heated to boiling under reflux and the progress of the reaction was followed by means of TLC (eluent: ethyl acetate/hexane 1/1: R$_f$ of the product: 0.24). After 2.5 h, the reaction mixture was cooled to 0° C. and poured cautiously with stirring into a 100 ml of a saturated sodium hydrogencarbonate solution. This mixture was then extracted 5 times with 100 ml of ethyl acetate each time. The combined organic phases were dried over Na$_2$SO$_4$ and concentrated by evaporation. Subsequent flash chromatography using Si60 silica gel (column 25×5.5 cm; hexane/ethyl acetate 3/1) gave 3.5 g (81%) of 2-cyano-2-methoxyacetamide as a colorless liquid which solidified on cooling.

| | |
|---|---|
| $^1$H NMR (CDCl$_3$): δ = | 6.85 (bs, 1H); 6.65 (bs, 1H); 4.65 (s, 1H); 3.63 (s, 3H). |
| $^{13}$C NMR (CDCl$_3$): δ = | 165.2 (C=O); 114.2 (C≡N); 70.6 (CH); 58.7 (CH$_3$). |

What is claimed is:

1. A process for preparing alkoxymalononitriles of the general formula

(I), where R$^1$ is C$_{1-6}$-alkyl or halogen-substituted C$_{1-6}$-alkyl, characterized in that the appropriate alkoxymalonamides of the general formula

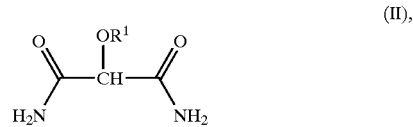

(II), where R$^1$ is as defined above are reacted with a dehydrating agent.

2. The process as claimed in claim 1, wherein the dehydrating agent used is trifluoroacetic anhydride, dibutyltin oxide, phosphorous oxychloride, phosphorus trichloride or phosphorus pentachloride.

3. The process as claimed in claim 2, wherein the dehydrating agent is used in quantities of from 0.5 to 6 molar equivalent per amide group of the alkoxymalonamide (II).

4. The process as claimed in claim 1, wherein the dehydration is carried out in a boiling solvent.

5. The process according to claim 1, wherein the dehydration takes place in the presence of a Lewis acid.

6. The process as claimed in claim 5, wherein the Lewis acid used is AlCl$_3$.

7. The process as claimed in claim 1 wherein R$^1$ is methyl or trifluoromethyl.

* * * * *